United States Patent [19]

Runnells et al.

[11] Patent Number: 4,592,896
[45] Date of Patent: Jun. 3, 1986

[54] COMBINATION STEAM AND UNSATURATED CHEMICAL VAPOR STERILIZER

[75] Inventors: Robert R. Runnells, Kaysville; Peter A. Haak, Salt Lake City; Rodney B. Larkin, Kaysville; Keith Vandervelden, Salt Lake City, all of Utah

[73] Assignee: MDT Biologic Company, Gardena, Calif.

[21] Appl. No.: 525,168

[22] Filed: Aug. 22, 1983

Related U.S. Application Data

[62] Division of Ser. No. 261,506, May 7, 1981, Pat. No. 4,447,399.

[51] Int. Cl.$^4$ .................... G05D 16/00; G05D 23/00
[52] U.S. Cl. ........................... 422/109; 422/95; 422/295; 422/113; 236/92 C; 220/203
[58] Field of Search .................. 422/3, 11, 25, 26, 33, 422/39, 113, 292, 295, 296, 95, 109; 236/92 C; 220/203

[56] References Cited

U.S. PATENT DOCUMENTS

| 478,871 | 6/1892 | Johnson | 422/113 |
|---|---|---|---|
| 2,069,820 | 7/1932 | Dodge | 422/33 |
| 2,497,201 | 2/1950 | Banner | 236/92 C |
| 4,146,570 | 3/1979 | Nagy | 422/299 |
| 4,203,943 | 5/1980 | Gillis et al. | 422/39 |
| 4,241,010 | 12/1980 | Baran | 422/39 |
| 4,259,293 | 3/1981 | Najarian et al. | 422/299 |
| 4,261,950 | 4/1981 | Bainbridge et al. | 422/27 |
| 4,309,381 | 11/1982 | Chamberlain et al. | 422/111 |
| 4,428,909 | 1/1984 | Yashiki et al. | 422/98 |
| 4,459,936 | 7/1984 | Karle | 422/26 |

FOREIGN PATENT DOCUMENTS

481373 10/1937 United Kingdom ............ 422/292

*Primary Examiner*—David L. Lacey
*Assistant Examiner*—Titus B. Ledbetter, Jr.
*Attorney, Agent, or Firm*—Trask & Britt

[57] ABSTRACT

A temperature sensor/pressure relief valve has a sensing end positioned within the pressure chamber of a sterilizer and an exhaust end positioned outside the pressure chamber. The temperature sensor is cooperatively adapted to a terminal apparatus at the sensing end to form a pressure relief valve.

3 Claims, 6 Drawing Figures

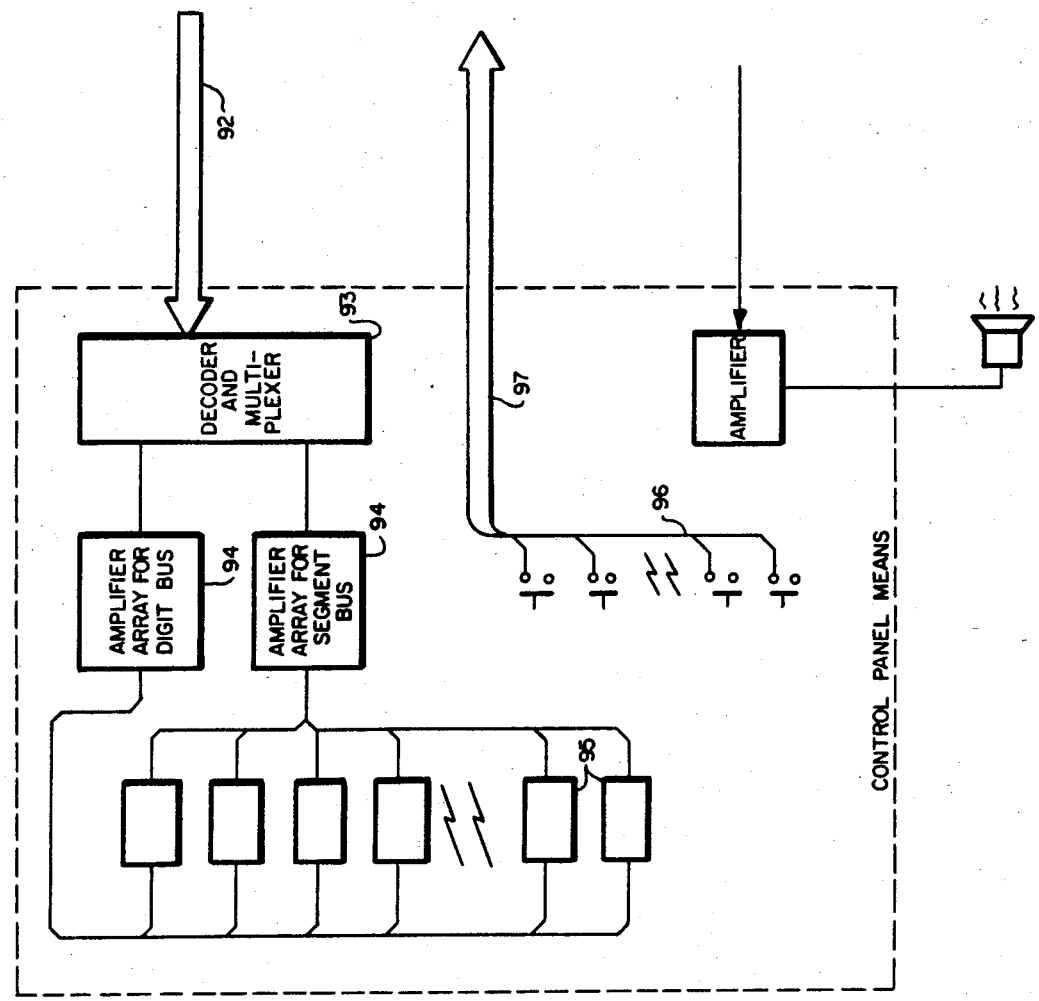

COMBINATION STEAM AND UNSATURATED CHEMICAL VAPOR STERILIZER

This is a division of application Ser. No. 261,506, filed May 7, 1981, now U.S. Pat. No. 4,447,399.

BACKGROUND OF THE INVENTION

1. Field:

This invention relates to the field of sterilization systems. More specifically, this invention comprises a combination unsaturated chemical vapor sterilization system and a steam sterilization system utilizing the same sterilizing chamber. It specifically provides a combination temperature sensor/pressure relief valve for such systems.

2. State of the Art:

As discussed in the pamphlet entitled "Principles and Practice of Unsaturated Chemical Vapor Sterilization", published by Aseptic-Thermo Indicator Medical-Surgical Division of the Parke, David & Co., of North Hollywood, Calif., there are four generally accepted sterilization systems: steam, dry heat, chemical agents and unsaturated chemical vapor. Traditionally, these sterilizing methods utilize separate devices to sterilize materials.

The steam sterilization autoclave is the most commonly used form of sterilization. Generally, the steam autoclave exposes materials to be sterilized to saturated steam at 121 degrees centigrade and 15 pounds per inch pressure for 12 to 15 minutes. The temperature and pressure may be varied to alter the exposure time necessary for sterilization. Pressurized steam in a vacuum has the advantage of quick penetration of items to be sterilized such as textiles. The moisture also has the advantage of more quickly killing spores. The disadvantage of steam is that it rusts and corrodes certain metals, dulling cutting edges of many instruments and requiring the drying of objects after the completion of the cycle. Also, certain plastics, rubbers and other materials sensitive to heat and moisture cannot practically be sterilized in a steam autoclave. Thus, one of the other types of sterilizers is required for these materials.

A dry heat sterilizer avoids the rusting and corroding problems caused by saturated steam. However, high temperatures, frequently at 160 to 170 degrees centigrade, for relatively long exposure times of two to four hours are required. Also, the dry heat tends to "stratify" or trap air in layers. The layers create air pockets which prevent the even exposure to heat.

One commonly used chemical sterilizer uses ethylene oxide. Ethylene oxide gas sterilizers are effective sterilizing equipment if sophisticated handling techniques are used. Pure ethylene oxide gas is flammable and toxic. Most gas sterilizers use a non-flammable mixture of twelve percent (12%) ethylene oxide gas and eighty-eight percent (88%) chloro and/or fluro methane gases. The main disadvantage of ethylene oxide sterilizers is the long sterilization times required—typically one to four hours exposure time plus additional time for aeration. Certain porous materials have aeration times as long as five to seven days. Ethylene oxide is also a known mutagen and carcinogen requiring extreme care in handling.

Another commonly used chemical sterilizer uses liquid alkaline gluteraldehyde. This disinfectant solution is desirable where higher temperatures will damage the materials to be sterilized. The disadvantage of gluteraldehyde sterilants is that they are unstable in solution. They must therefore be mixed prior to use. Also, the effective life of the solution is approximately two weeks. Exposure times of a minimum of ten hours are required, and items must be thoroughly rinsed to prevent damage to skin or other sensitive tissues.

The unsaturated chemical vapor system is used primarily to sterilize metal instruments and materials. The unsaturated chemical vapor system uses heat, water and chemical synergisms. Moist heat is used to induce chemical reactions which denature and coagulate proteins by catalysis in the presence of water. To prevent the rusting, corroding and dulling effect of water, various solutions of alcohols, acetones, ketones and formaldehyde are used with water to reduce the water content below approximately fifteen percent (15%) by weight. Ethyl alcohols and formaldehydes in combination especially act as effective disinfectants. An example of these chemical solutions is the solution of isopropyl alcohol, methyl alcohol, ethyl alcohol, formaldehyde, acetone, methyl ethyl ketone, butanol, water and fragrances produced and sold by MDT Chemical Company of Gardena, Calif., under the trademark "Vapo-Steril". The "Vapo-Steril" percentages for isopropyl alcohol, methyl alcohol, ethyl alcohol and butanol are approximately 82%; formaldehyde approximately 1%, and water, ketone and acetone approximately 17%.

The unsaturated chemical vapor sterilizer mechanically introduces a fixed amount of chemical solution into a preheated, chamber. The chamber is pre-evacuated of air prior to the introduction of the chemical solution. The air is evacuated because it can interfere with sterilization. Also, the emptying of the air from the chamber enables higher concentrations of sterilizing vapors to be attained within the chamber. Evacuation is generally accomplished by applying a vacuum of minus 20 to 30 mm of mercury. This solution generally vaporizes at approximately 78 degrees centigrade. When heated to approximately 131 degrees centigrade, plus or minus five degrees centigrade, a minimum sterilizing pressure of approximately 20 pounds per square inch is attained. This temperature and pressure is maintained for approximately 20 minutes.

Sterilization is begun immediately upon admission of the chemical solution into the preheated chamber. The chemical solution condenses on the materials to be sterilized which have not been preheated. Preferably, this is accomplished by loading the sterilizer carrier tray with items to be sterilized which have been rinsed in cold water and towel dried. The tray is then placed in the preheated sterilization chamber and the chemical solution immediately introduced. The solution condenses on the colder materials and starts bactericidal activity and rehydrating desiccated spores. Rehydrated spores are more susceptible to sterilization in shorter periods of time. As the chamber is heated, it is pressurized to approximately 20 pounds per square inch. The condensed solution vaporizes, resulting in increased sterilization activity.

Following sterilization, the chamber is depressurized and air is pumped through a sterile filter into the chambers and serves to purge residual chemicals from the chamber into a tank and finally through a chemical filter.

The unsaturated chemical vapor sterilizer has the advantages of shortened sterilizing times and prevents rusting, corroding and dulling of metal objects. The vapor sterilizer has the disadvantage of slowly penetrating textiles and similar woven materials for sterilization. Also, it cannot be used with objects such as certain rubber and plastic objects which are attacked by the chemical solutions. Nor can it be used with objects which cannot withstand a temperature of 131 degrees centigrade.

Thus, to sterilize a wide variety of materials, different sterilizers were required depending upon the necessary sterilizing conditions. Several attempts to combine pre and post sterilizing operations utilizing the same sterilizing chamber have been attempted with varying degrees of success. Young et al, U.S. Pat. No. 4,193,818, entitled "Combined Ultrasonic Cleaning and Biocidal Treatment in a Single Pressure Vessel", combined an ultrasonic cleaning circuit with a biocidal sterilizer. The ultrasonic cleaning circuit's function was to prepare items for sterilizing by first removing soil, blood, debris and other extraneous materials before the sterilizing cycle is operated. After the ultrasound treatment, the chamber is drained and the articles to be sterilized rinsed. A biocidal fluid, e.g., steam, is then injected into the sterilizing chamber to sterilize the articles placed therein. This invention does not utilize the same sterilizing chamber for different sterilizing operations.

Other devices utilize the same sterilizer chamber for a drying cycle after a steam sterilization cycle. The dry heat cycle is carried on in the sterilizer vessel at room pressures. This type of device rusts, corrodes and dulls certain metal objects. Use of the drying cycle at room pressures also results in extremely long drying times.

Another device utilizes the same sterilizing chamber for steam sterilizing, or alternatively, for ethylene oxide sterilizing. Presumably, the ethylene oxide cycle is used for objects which are sensitive to heat. However, the ethylene oxide cycle takes a long time to operate, and is very toxic and flammable requiring extreme care in handling.

It is important to control the temperature and pressure conditions within the sterilizer's chamber in all of the previously described sterilizers.

SUMMARY OF THE INVENTION

The present invention provides a temperature sensor/pressure relief valve for mounting in association with the pressure chamber in a sterilizer. One embodiment includes a sterilizer which comprises a fixed volume impervious sterilizing chamber. Access means, such as the pressure chamber latch and door, described in U.S. Pat. No. 3,473,693, entitled "A Pressure Chamber Cover Latch", are included to enable a user to insert materials into the chamber for sterilizing. A heating element is mounted in association with the interior of the chamber to heat said chamber. A source of sterilizer chemicals, e.g., a chemical reservoir, is included to hold various chemical solutions. One preferred chemical solution for use under temperatures exceeding pressures above 15 pounds per square inch is the vapo-steril solution previously discussed. Another preferred chemical solution is a solution of approximately seventeen to twenty percent formaldehyde, approximately forty-five to fifty percent isopropyl alcohol and approximately thirty to thirty-eight percent water. This solution is particularly suited for low temperature chemical vapor sterilization for use with temperature sensitive items such as endoscopes and catheters. The selection of the type of chemicals for unsaturated chemical sterilization and the temperatures and pressures required are generally discussed in *Accepted Dental Therapeutics*, 37th Ed., January 1977, published by American Dental Association, Chicago, Ill. Another reference, *Disinfection, Sterilization and Preservation*, by Seymour S. Block, published by Lea & Febiger (Philadelphia, 1977) discusses the preferred steam pressures and temperatures required for steam sterilization.

A source of water is also included, e.g., a water reservoir. Transport means in communication with the source of sterilizing chemicals and the source of water are also in communication with the interior of the chamber, e.g., tubing. By elevating the sources of water and sterilizer chemicals, the sterilants may be delivered into the chamber by gravity flow. The transport means includes a valve system to selectively convey a measured quantity of sterilizing liquid into the chamber, e.g., the motorized valve described in U.S. Pat. No. 3,650,305, "A Valve for Dispersing Measured Quantities of Liquids". This motorized three-way valve effectively delivers a measured quantity of liquid into the chamber at a given time.

Switching means are included, such as a microcircuit processor, having interface means, logic means and a control panel. The switching means are operably associated with a power source to drive the transport means and provide power for the heating element. Thus, the switching means control the gaseous or liquid state of the sterilizing chemicals or water and the temperature and pressure within the chamber at a given time according to the preference of the user. By using a fixed volume vessel and injecting a measured quantity of sterilizing fluids into the chamber, the pressure and temperature can be controlled by varying the output of the heating element. Other variations also include a pressure regulator to directly control the pressure, a temperature regulator to control the temperature, and/or purging means, e.g., vacuum pump, to evacuate the chamber.

In one embodiment, a reversible pump with valve means is associated with the interior of the chamber to selectively evacuate or purge said chamber. In another embodiment, the pump includes gate means associated with passageways in communication with the interior of the chamber, to selectively evacuate or purge the chamber through the action of the pump.

Generally, the switching means includes interface means, e.g., circuitry operably associated with the transport means, heating element, power source and, where included, the pressure regulator, temperature regulator and purging means. The interface circuitry not only controls the various means and elements, but may generate electronic signals reflecting the temperature, pressure and sterilizer chemical or water composition within the chamber at a given time. Logic means, e.g., a microcircuit, are associated with the interface means to direct at a given time whether sterilizer chemicals or water are delivered into the chamber, and specify the temperature and pressure to be maintained within the chamber. The logic means also translates any electronic signals received from the interface means reflecting the temperature, pressure and sterilant composition within the chamber. These translated signals are sent to control panel means cooperably associated with the logic means. The control panel means generates various audible and visual signals to inform the user as to the sterilizing conditions within the chamber at a given time. The control panel means also enables a user to program the logic means to determine which sterilant, temperature and pressure should be maintained within the chamber at a given time.

Another embodiment includes two sources of sterilizer chemicals for unsaturated chemical vapor sterilization along with a water source. The one source of chemicals is designed for low temperature sterilization at approximately 140 to 160 degrees Fahrenheit and pressures of approximately 0 to 10 pounds per square inch. A preferred low temperature chemical sterilizer is a solution of approximately 17 to 20 percent formaldehyde, approximately 45 to 50 percent isopropyl alcohol, and approximately 30 to 38 percent water.

The other source of chemicals is designed for high temperature sterilization at approximately 250 to 300 degrees Fahrenheit and pressures of approximately 20 to 40 pounds per square inch. A preferred high temperature chemical sterilizer is a solution marketed under the trade name "Vapo-Steril" previously discussed.

The two chemical sources and water source are interruptedly connected with the sterilizer chamber in the same manner described above to deliver a preselected sterilant and maintain a preselected temperature and pressure within the chamber at a given time.

To ensure that the proper sterilizing temperatures are maintained and that the pressure limits of the chamber are not exceeded, a combination temperature sensor/pressure relief valve is mounted within the interior of the chamber. The temperature sensor/pressure relief valve comprises a hollow impervious walled housing having an open sensing end and an open exhaust end. The sensing end has a beveled open cross-sectional diameter less than the cross-sectional diameter of the housing. The sensing end is located within the chamber such that the open exhaust end is in communication with the ambient environment exterior to the chamber. An impervious temperature sensor is operably associated with the switching means and slideably mounted within the housing near the sensor end. The cross-sectional diameter of the sensor is less than the diameter of the housing to enable gases, vapors, fluids and steam to pass therebetween. However, the cross-sectional diameter of the sensor is greater than a cross-sectional diameter of the sensing end and structured such that a seal is formed when the sensing end is contacted by the temperature sensor. Means to urge the temperature sensor against the sensing end at a predetermined pressure are included. Exceeding the predetermined pressure within the chamber causes the sensor and sensing end to separate. As the predetermined pressure is exceeded, the sensor and the sensing end seal is broken releasing sterilizing fluids, vapors or steam from the chamber. It is preferred that the temperature sensor be insulated from the housing to provide a truer temperature reading within the interior of the chamber. For example, an O-ring made of an insulating material may be sealingly mounted to the housing sensing end. The O-ring has an open diameter less than the diameter of the sensor. It is structured to form a seal with the sensor when the sensor contacts the O-ring. In one embodiment, the means to urge the temperature sensor against the sensing end comprises a spring attached to the housing. The spring has a preselected spring constant to insure that specified pressure limits within the chamber are not exceeded.

In a preferred embodiment, the temperature sensor/pressure relief valve has a flexible housing which may be bent to maintain the sensor in a preselected position within the chamber during sterilization. The use of a flexible housing enables the sensor to be positioned near the center of a load of materials to be sterilized. By measuring the temperature near the center of a load, sterilization is assured since the center of the load generally receives the least heat exposure.

Because of various federal and state sterilization requirements, recording means may be associated with the logic means to maintain a record of the type of sterilant, the temperature and pressure within the chamber, and the time that the materials are exposed to be sterilized. The selection of the parameters to be recorded is generally governed by federal and state requirements. These requirements are well known to those familiar with the art, and are periodically specified by authorized agencies such as the Joint Commission for Accreditation of Hospitals. To comply with other various state and federal agencies, the humidity within the chamber at a given time may also be recorded.

It is also preferable to include various safety features, e.g., latch locking switch, to insure that the chamber is sealed during sterilization.

Filter means are generally associated with the chamber when chemical sterilants are purged and vented. Typically, a filter is associated with the purging means to separate chemicals that are evacuated from the chamber. One filter marketed under the trademark "Purafil" manufactured by Purafil Company, P.O. Box 80434, of Chamblee, Ga., is preferred for use with the Vapo-Steril chemicals. The Purafil filter is primarily comprised of active alumina impregnated with potassium permanganate. Other filters to comform with federal and state standards may be used. These filters are generally required to protect the user from coming into contact with purged sterilizer chemical vapors.

DESCRIPTION OF THE DRAWINGS

FIG. 6 is a schematic view of the display panel;

DESCRIPTION OF THE ILLUSTRATED EMBODIMENTS

Figure 1:
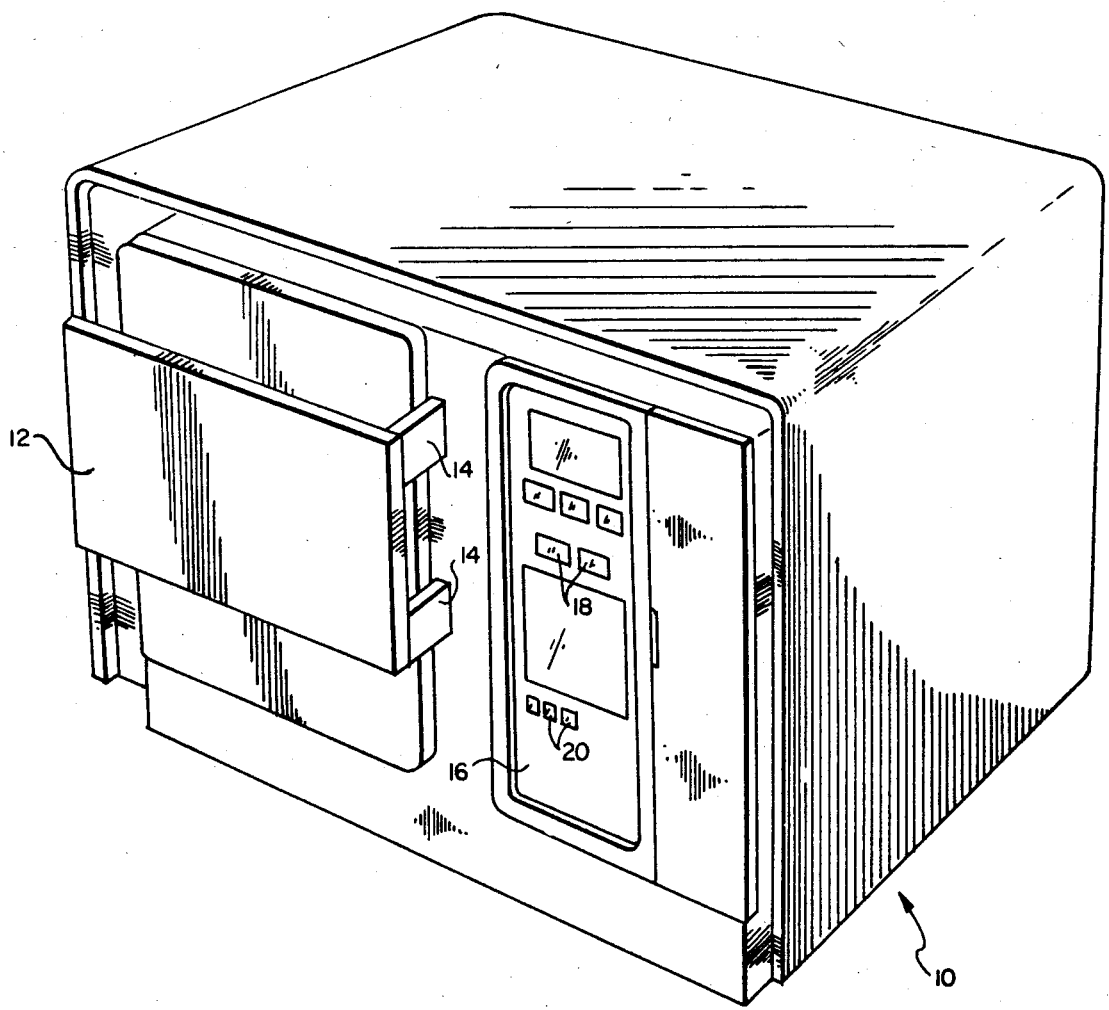
FIG. 1 is a perspective view of one embodiment of applicant's invention.

FIG. 1 is a perspective view of one embodiment of the combination steam and unsaturated chemical vapor sterilizer 10. The access means are shown as a hinged door 12. The door 12 includes a safety latch 14 to insure that the chamber (not shown) is sealed before sterilization. The control panel 16 is shown with various push buttons 18 for a user to select and program the sterilizing cycle. Also shown are signal lights 20 showing the conditions within the insides of the chamber 22 (not shown).

Figure 2:
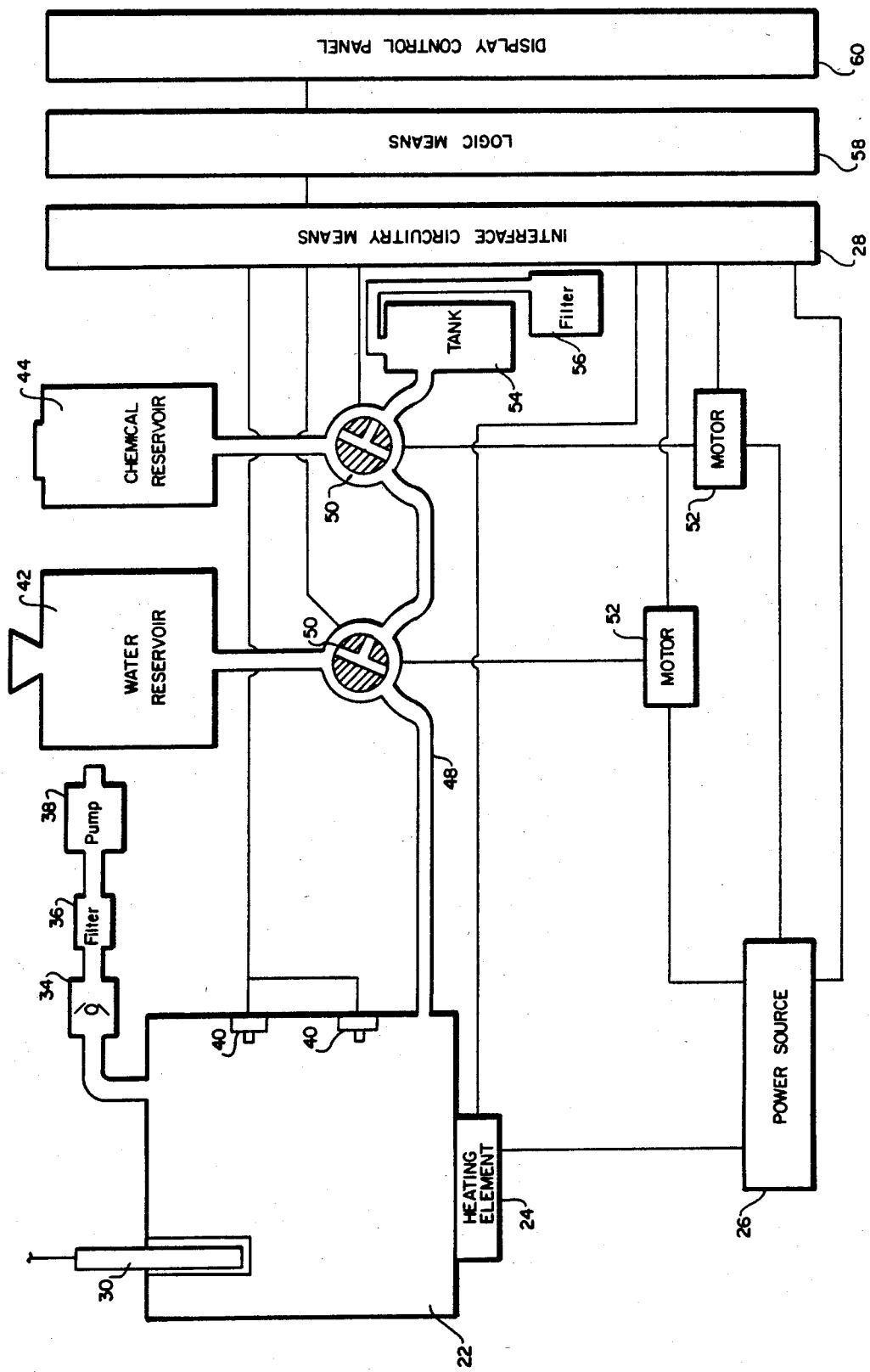
FIG. 2 is a schematic view of applicant's invention.

FIG. 2 is a schematic view of applicant's invention. A sterilizing pressure chamber 22 is associated with a heating element 24. The heating element 24 is powered by a power source 26. Both the heating element 24 and the power source 26 are controlled by switching means including the interface circuitry means 28. A temperature sensor/pressure relief valve 30 is attached to the chamber 22 such that the temperature sensor (not shown) is located within the interior of the chamber 22 and its exhaust end (not shown) is exterior to the chamber 22. Evacuation means 32, shown as a one-way check valve 34 associated with a sterilizer filter 36 and a reversible pump 38, may be mounted in communication with the interior of the chamber 22. The evacuation means 32 are controlled by the interface circuitry means 28. The evacuation means 32 evacuate the chamber 22 of air and/or sterilants. In the first cycle, the pump 38 evacuates the chamber 22 of air. After sterilization has completed, the pump 38 is reversed to create a positive pressure within the chamber 22 by drawing in air through the sterile air filter 36. Sterilants are generally vented from the chamber 22 by purging means shown as the tank 54 and filter 56 in communication with the chamber through passageway 48. The pressure in the chamber 22 forces the sterilants through the passageway 48 into the tank 54 and through the filter 56 to the ambient environment external to the chamber 22.

Safety switches 40 may be included. The switches 40 are mounted external to the chamber 22. The switches 40, as mounted, contact the hinged door 12 (not shown) when closed. The switches 40 are communicably associated with the interface means 28. If the hinged door 12 is not closed sealing the chamber 22, the sterilizer 10 is not operable.

A water reservoir 42 and sterilizer chemical reservoir 44 are associated with the sterilizer 10. Transport means, shown as common passageway 48 and two motorized three-way valves 50, interruptedly connect the water reservoir 42 and chemical reservoir 44 with the interior of the chamber 22. The three-way valves 50 are controlled by a motor 52. The motors 52 are connected to the power source 26 and controlled by the interface circuitry means 28. The valves 50 have an open position and a closed position to prevent or allow sterilants to pass. The valves 50 are synchronized such that either water or chemical sterilants is delivered through the passageway 48 into the chamber 22 at a given time. The valves 50 have a third position to shut off the flow of fresh sterilants into and drain used sterilants from the chamber 22 through the valves 50 and passageway 48 into the tank 54. In this third position, the valves 50 shut off the water reservoir 42 and chemical reservoir 44. The tank 54 has the filter 56 to release pressure buildup in the tank 54 and to prevent residual chemicals from entering the ambient air.

The interface circuitry means 28 is operably associated with the temperature sensor/pressure relief valve 30, the safety latch 14, the heating element 24, the power source 26, the motors 52 and the motorized valves 50 to control them in response to directive signals. The interface circuitry means 28 may also generate electronic signals reflecting the temperature, pressure and sterilizer chemical or water compositions within the chamber at a given time.

Logic means 58 are communicably associated with the interface circuitry means 28 to provide directive signals in response to programmed instructions. Also, the logic circuitry means 58 may translate the electronic signals generated by the interface circuitry means 28.

A display control panel 60 is associated with the logic means. The control panel 60 provides program instructions to the interface means 28. The control panel 60 also responds to the translated signals of the logic circuitry means emitting audio or visual signals for a user to determine the temperature, pressure and sterilant composition within the chamber 22.

Figure 3:
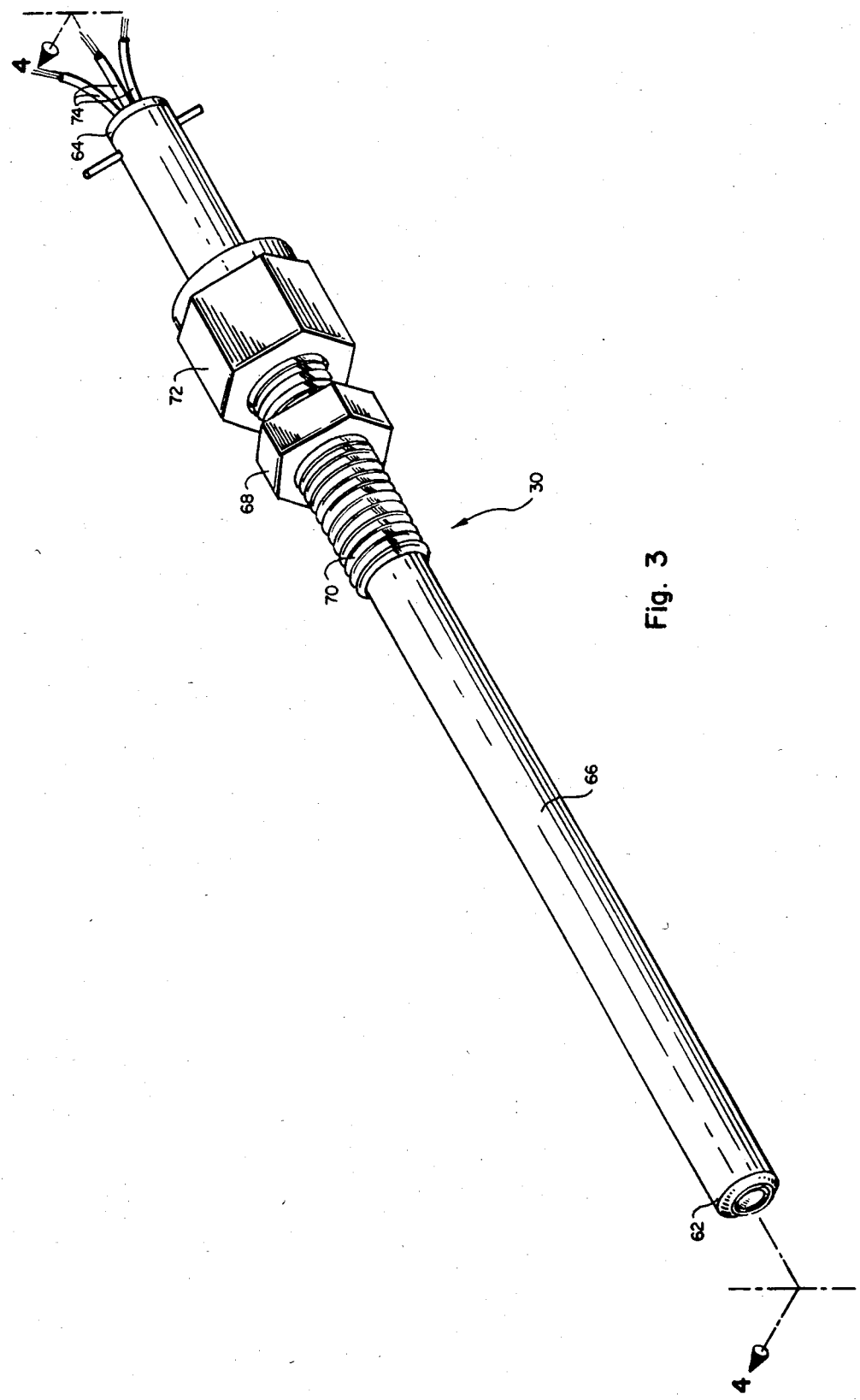
FIG. 3 is a perspective view of a combination temperature/pressure relief valve.

FIG. 3 is a perspective view of a preferred combination temperature/pressure relief valve 30. The valve 30 has a sensing end 62 and an exhaust end 64. The valve housing 66 is hollow with the sensing end 62 beveled. A threaded screw fitting 68 is slideably mounted along the exterior of the housing 66. The fitting 68 has a male end 70 which secures to a corresponding female threaded slot leading into the chamber 22 (not shown). When the male end 70 is secured to the chamber 22, the sensing end 62 is sealed within the interior of the chamber. A locking nut 72 may be used in association with the fitting 68 to insure the seal. Various wire leads 74 connect the valve 30 with the interface means 28.

Figure 4:
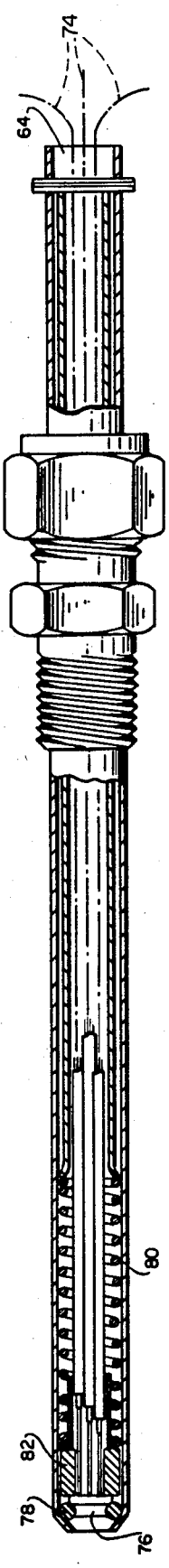
FIG. 4 is a cross-sectional view of the combination temperature/pressure relief valve.

FIG. 4 is a cross-sectional view of the combination temperature/pressure relief valve 30 shown in FIG. 3. A temperature sensor 76 including means (leads 74) for electronically connecting it to interface circuitry means 28, is slideably mounted within the housing 66. The diameter of the temperature sensor 76 is less than the housing 66 enabling gases to pass therebetween. However, the diameter of the temperature sensor 76 is less than the beveled sensing end 62 of the housing 66. When urged against the sensing end 62, the temperature sensor 76 and the sensing end 62 form a seal. A silicone rubber O-ring 78 may be included to isolate the temperature sensor 76 from the sensing end 62 to give a more accurate reading of the temperature within the chamber 22.

As shown, a spring 80 mounted within the housing 66 urges the temperature sensor 76 against the O-ring 78. As the spring constant pressure is exceeded by pressure buildup in the chamber 22, the temperature sensor 76 retracts. The seal between the temperature sensor 76 and the O-ring 78 is thus broken. Gases, vapors and fluids are released through the broken seal and vented out of the chamber through the exhaust end 64. A spacer 82 may be inserted between the spring 80 and the temperature sensor 76. The spacer 82 thermally isolates the temperature sensor 76 from heat transmitted through the spring 80.

Figure 5:
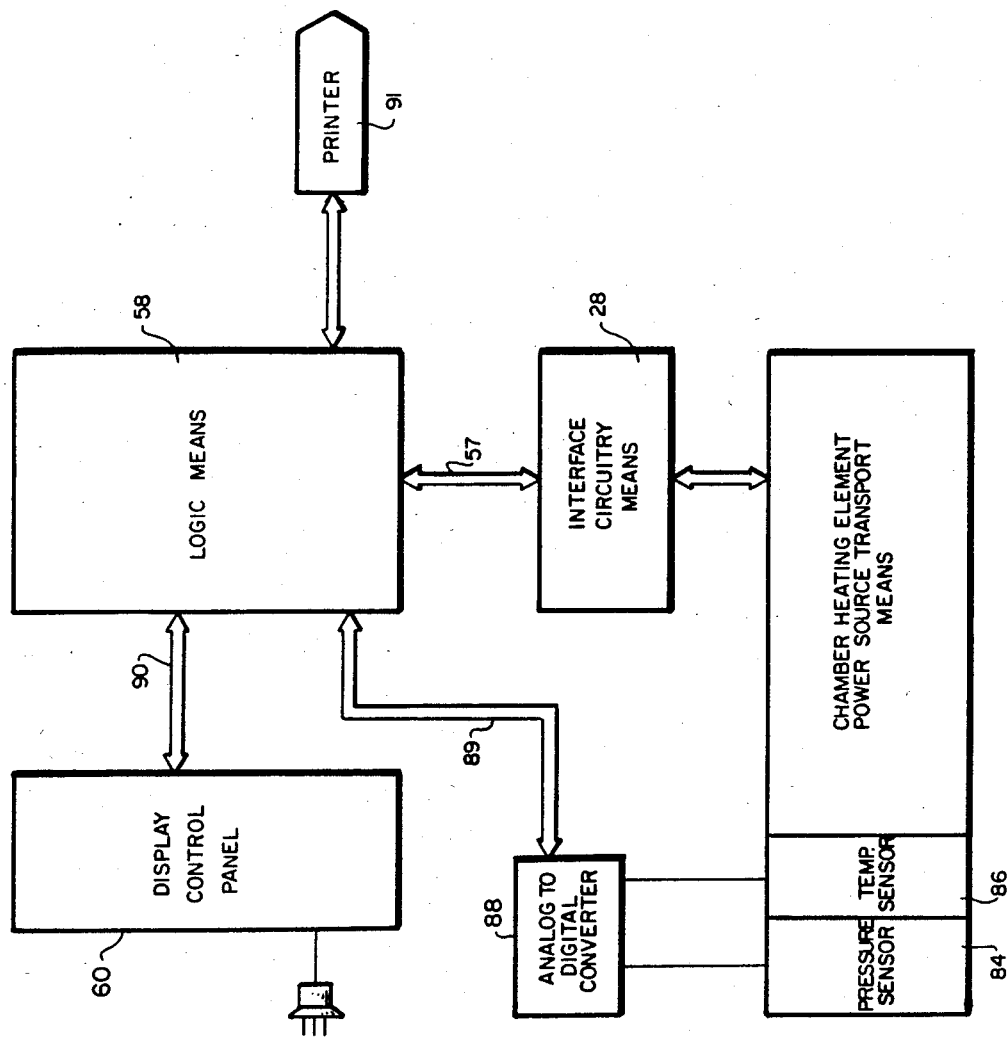
FIG. 5 is a schematic view of the switching means.

FIG. 5 is a schematic view of a preferred embodiment of the switching means 27. The switching means 27 is comprised of three main circuitry functions: interface circuitry means 28, logic means 58 and the display panel 60. The interface circuitry means 28 controls the temperature, pressure and sterilant composition within the chamber 22 at any given time. The interface circuitry means 28 is cooperably associated with the chamber 22, heating element 24, power source 26 and transport means 46 as previously discussed.

The interface circuitry means 28 generates signals to the logic means 58 as to the state of various preselected parameters, e.g., temperature, pressure, etc. The logic means 58 provides directive signals to the interface circuitry means 28 for controlling the various elements cooperably associated with the interface circuitry means 28. Thus, a bidirectional bus 57 is formed.

A pressure sensor 84 and a temperature sensor 86 are mounted within the chamber 22. An analog to digital converter 88 is connected to the pressure sensor 84 and temperature sensor 86. A bidirectional bus 89 connects the logic means 58 and the converter 88.

The logic means 58 is cooperably associated with a bidirectional bus 90 to the display control panel 60, as previously discussed.

A printer 91 is associated with the logic means 58 to record certain preselected parameters, e.g., the temperature, pressure, type of sterilant and exposure times of articles placed within the chamber 22 for sterilization.

FIG. 6 is a schematic view of the display control panel 60. Translated signals from the logic means 58 come into the control panel 60 by bus 92 and are received by a decoder and multiplexer 93. Here the translated signals are decoded and amplified. They are then transmitted by conventional bus circuits 94 to display elements 95. The control panel 60 also contains control buttons 96 to program the sterilization cycle perferred by the user. When the control buttons 96 are activated, directive signals are transmitted by bus 97 to the logic means 58.

Reference in this disclosure to details of the illustrated embodiments is not intended to restrict the scope of the appended claims, which themselves recite those features regarded as essential to the invention.

We claim:

1. A temperature sensor/pressure relief valve having a sensing end and an exhaust end mounted to a pressure chamber of a sterilizer so that the sensing end is inside the chamber and the exhaust end is outside the chamber, comprising:

a hollow, impervious cylindrical housing having a first end comprising said sensing end with a terminal aperture of diameter less than the inside diameter of the housing, and an open second end comprising said exhaust end in communication with an ambient environment exterior to the chamber;

an impervious temperature sensor including means for electronically connecting it to interface circuitry means, said temperature sensor being slidably mounted within the housing near said sensing end so that it is positioned, selectively, to make contact with said terminal aperture, the cross-sectional diameter of the temperature sensor being less than the inside diameter of the housing to allow gases, vapors, fluids and steam to pass therebetween, but greater than the diameter of said terminal aperture, so that a seal is formed when the temperature sensor contacts said terminal aperture; and means for urging the temperature sensor against the sensing end until the pressure within the pressure chamber exceeds a predetermined pressure, thereby causing the temperature sensor to separate from the terminal aperture, partially releasing sterilizing chemicals, fluids, vapors or steam through said terminal aperture to said ambient environment until the pressure is reduced to or below the predetermined pressure.

2. A temperature sensor/pressure relief valve according to claim 1, including means for thermally isolating the temperature sensor from the housing.

3. A temperature sensor/pressure relief valve according to claim 1, wherein the means for urging the temperature sensor against the sensing end comprises a hollow cylindrical compression spring mounted within the housing, said spring having a preselected spring constant.

* * * * *